April 30, 1957 R. H. F. MANSKE Plant Pat. 1,595
DICENTRA PLANT
Filed Sept. 17, 1956
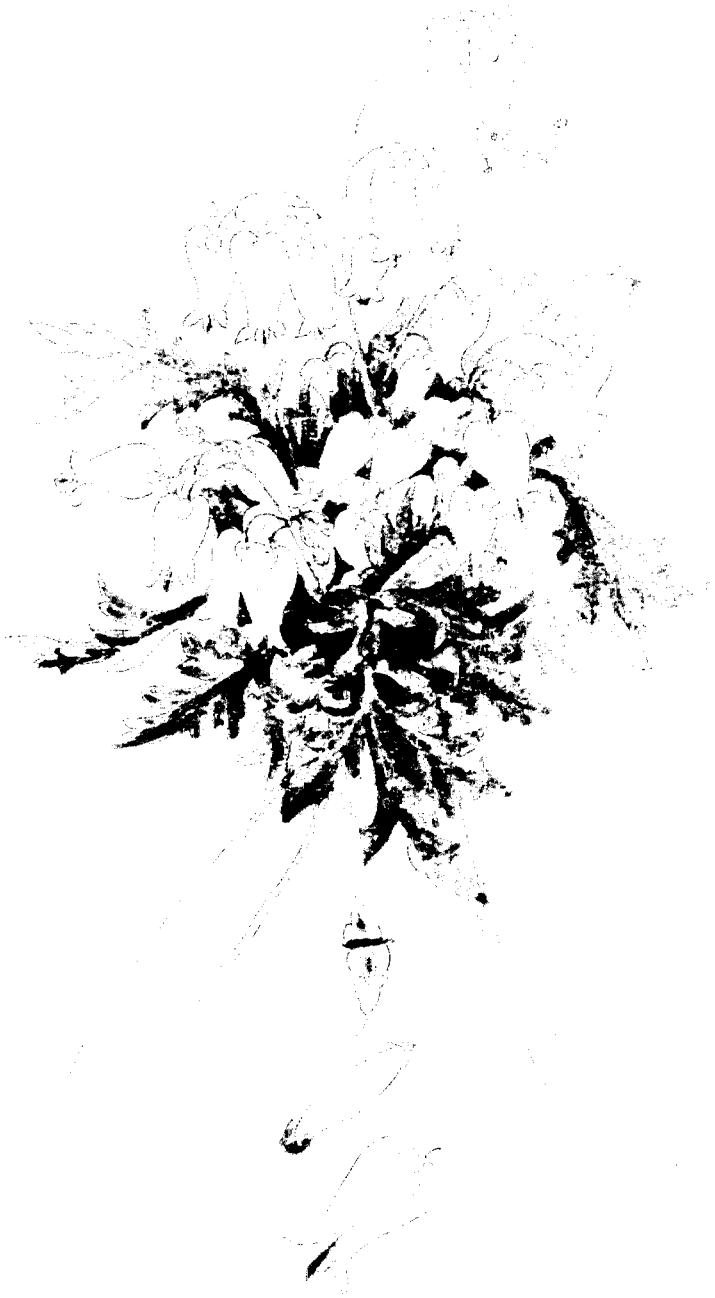
WITNESS
Addison E. Avery
INVENTOR
Richard H. F. Manske,
by: John H. Grounds,
his ATTY.

United States Patent Office

Plant Pat. 1,595

Patented Apr. 30, 1957

1,595

DICENTRA PLANT

Richard H. F. Manske, Guelph, Ontario, Canada, assignor to John J. Grullemans, Cleveland, Ohio Application September 17, 1956, Serial No. 610,428

1 Claim. (Cl. 47—60)

This invention relates to a new and distinct variety of Dicentra plant.

The new variety was first developed by me at Guelph, Ontario, Canada, and was asexually reproduced by me at Guelph, Ontario, Canada, by root division.

The new variety was developed in the following manner: A *Dicentra oregana* Eastwood plant, as a seed parent, was crossed with a *Dicentra eximia* (Ker) Torrey Plant, as the pollen parent. Neither of these parent plants is patented.

Seeds from this crossing were planted in beds in close proximity to each other and allowed to cross pollinate freely. Seeds from this first mass planting and natural cross pollination were then planted in beds in close proximity and exposed to open pollination. Seeds from this second mass planting were planted and the new variety was selected from the resulting seedlings.

*The drawing*

The new variety is illustrated in the drawings in which the large central illustration shows a group of typical leaf and flower stalks of the plant while in bloom and the three smaller illustrations therebeneath show, from top to bottom, a single bangle in bottom plan view, side elevation, and front elevation, respectively.

Color references herein are to the Maerz & Paul Dictionary of Color.

*The root of the plant*

The present new variety of Dicentra plant has the usual fibrous roots of the usual size for Dicentra plants. The roots are resistant to both wetness and drought, and, when unprotected, have withstood temperatures as low as 20° below zero, Fahrenheit, in Guelph, Ontario, Canada.

*The exposed plant structure*

The exposed part of the plant is herbaceous and bushy, reaching a height of about 14″ to 18″ with a spread of 16″ to 20″ when the plant is from two to three years old. The exposed part of the plant is quite symmetrical and regular in outline.

The plant is a vigorous grower. Its foliage dries out at lower temperatures, whether the plant is protected or not, but in general the foliage is resistant to drought and wet seasons. So far as can be observed, none of the plants of this variety has ever been damaged by insect pests. The plant produces its best foliage when growing in moderate sun or partial shade in well-drained rich humus soil.

The plant blooms best in a temperature climate preferring a range from Virginia, United States of America, northward to Ontario, and Quebec, Canada. It blooms best in a partial shade in a rather wet cool season. The quality of the blooms is best when the plant is growing in a well-drained, though moist, soil. The plant is essentially a cooler climate plant and does best in short daylight. The cutting of the blooms does not appear to have any effect on the blooming characteristics.

*The parts of the exposed plant*

The main stalks of the plant are generally uniform in color, ranging from oasis green, comparable to Plate 20–L–2 to French Beige or Sunburn, comparable to Plate 13–A–7. They range from approximately 12″ to 18″ in length and have a smooth surface texture. They are grouped and diverge upwardly from the roots, being generally upright and downwardly recurvant slightly at the top. A two year old plant usually has about 30 to 40 stalks.

*Foliage*

The foliage is generally dense and lacey, the leaf arrangement being compound. The leaves are basal. They are abundant and of the usual size. In shape, they are compound pinnate with serrated margins and acute apices, and are tapering at the base. They are of medium thickness with smooth upper and lower faces. On the upper faces they are a Peridot green, comparable to Plate 22–L–6. On the underside they are a green comparable to Plate 20–E–4. Their persistency on the plant is excellent.

The leaf stems average from 10″ to 12″ in length and have a smooth surface texture. They are free from stipules.

*Buds and blooms*

The buds are terminal and supported pendantly. They are of the usual surface texture and have the sepals like those of other varieties of Dicentra plants. The pedicels or individual stalks of the flowers are pale green, comparable to Plate 21–K–1. They are of medium strength. The present variety blooms very strongly in the spring before the *Dicentra eximia,* lasting well into July, and again in the fall as freely as in the spring, with intermittent blooming periods between the spring and fall seasons. The blooms are somewhat larger than the blooms of the *Dicentra oregana* or the *Dicentra eximia* ancestors, being about double the size of the common bleeding heart plant. Their fragrance ranges from fair to none.

The permanence of the blooms on the plant is excellent and when cut is fair. Young plants bear somewhat less abundantly than young Dicentra plants of the variety known as Bountiful and described in Plant Patent 1,198 of June 23, 1953. When the plants are three years old, however, they are as productive of blooms as the Dicentra plant Bountiful.

The genital organs and fruit of the new variety are usual, the seeds being small and reniform.

The plant adapts itself well to various latitudes, climates and soils. It is more robust than either the *Dicentra oregana* or the *Dicentra eximia* ancestors and, owing to its partial sterility, the plant blooms more profusely and for a longer period of time than either of its original ancestors. Its predominate feature, distinguishing it from any of its ancestors and the Dicentra variety of Plant Patent No. 1,198, known as Bountiful, is the color of the large bangles.

The main body of the flowers ranges from a pale pink, comparable to Plate 50–B–1, through Plate 50–D–5 to 50–F–5, the bottom outwardly flaring tips or spurs being a crystal grey, comparable to Plate 53–A–2. The wing-like section formed by the crests of the inner petals and extending forwardly and rearwardly of the bangle at the bottom is a dull purple or violet comparable to Plate 54–H–4. The small triangular portion appearing at the lower tip of the bangle and disposed centrally between the outer petals and extending laterally of the bangle, formed by the inner petals adjacent their crests, is a dull purple or violet, comparable to Plate 54–C–4.

The color of the heart-like cap at the juncture of the stem and the bangle is Fallow, comparable to Plate 12–B–5. These caps are hardly noticeable.

The coloring of the bangles is very distinctive and results in very attractive individual bangles and blooms, and in a very attractive general tonality of the plant when viewed from a distance.

Having illustrated and described my new variety of Dicentra plant, I claim:

The new variety of Dicentra plant herein shown and described.

No references cited.